(12) United States Patent
Smith (10) Patent No.: US 9,339,410 B2
(45) Date of Patent: May 17, 2016

(54) ORAL MOTION PRESERVATION DEVICE (71) Applicant: SILVERFOX DENTAL & ORTHO, LLC, Sparks, MD (US)

(72) Inventor: Brian Francis Smith, Baldwin, MD (US)

(73) Assignee: SilverFox Dental & Ortho, LLC, Sparks, MD (US)

( * ) Notice: Subject to any disclaimer, the term of this patent is extended or adjusted under 35 U.S.C. 154(b) by 0 days.

(21) Appl. No.: 14/622,024

(22) Filed: Feb. 13, 2015

(65) Prior Publication Data

US 2015/0223969 A1    Aug. 13, 2015

Related U.S. Application Data

(60) Provisional application No. 61/939,586, filed on Feb. 13, 2014.

(51) Int. Cl.
| | |
|---|---|
| *A61F 5/56* | (2006.01) |
| *A61C 7/36* | (2006.01) |
| *A63B 71/08* | (2006.01) |
| *A61C 7/08* | (2006.01) |

(52) U.S. Cl.
CPC . *A61F 5/566* (2013.01); *A61F 5/56* (2013.01); *A61C 7/08* (2013.01); *A61C 7/36* (2013.01); *A61F 2005/563* (2013.01); *A63B 71/085* (2013.01)

(58) Field of Classification Search
CPC ..... A61F 5/56; A61F 5/566; A61F 2005/563; A63B 71/085; A61C 7/08; A61C 7/36
USPC ................... 128/848, 859, 861, 862
See application file for complete search history.

(56) References Cited

U.S. PATENT DOCUMENTS

| | | | |
|---|---|---|---|
| 5,031,611 | A | 7/1991 | Moles |
| 5,313,960 | A | 5/1994 | Tomasi |
| 5,365,945 | A | 11/1994 | Halstrom |
| 5,427,117 | A | 6/1995 | Thornton |
| 5,467,783 | A | 11/1995 | Meade |

(Continued)

FOREIGN PATENT DOCUMENTS

WO        2015123528  A1     8/2015

OTHER PUBLICATIONS

International Search Report and Written Opinion for International Application No. PCT/US2015/015833, mailed May 14, 2015, 16 pages.

*Primary Examiner* — Keri J Nelson
(74) *Attorney, Agent, or Firm* — Brake Hughes Bellermann LLP (57) ABSTRACT

A device for the treatment of bruxism may include an articulation plate worn on one of the upper or lower jaw and coupled to a bite plate worn on the other of the upper or lower jaw. Posts extending from one of the bite plate or articulation plate into housings in the other of the bite plate or articulation plate may couple the bite plate and articulation plate. The posts may include a solid, flexible material to allow for relative movement of the coupled bite plate and articulation plate. First articulating components on one of the bite plate or articulation plate may engage second articulating components on the other of the bite plate or articulation plate to allow for 360 degree articulating motion between the bite plate and articulation plate. A damper may adjust a distance between teeth received in the bite plate and teeth received in the articulation plate.

22 Claims, 9 Drawing Sheets

(56) References Cited

U.S. PATENT DOCUMENTS

| | | |
|---|---|---|
| 5,499,633 A | 3/1996 | Fenton |
| 5,536,168 A | 7/1996 | Bourke |
| 5,611,355 A | 3/1997 | Hilsen |
| 5,682,903 A | 11/1997 | Meade |
| 5,755,219 A | 5/1998 | Thornton |
| 5,823,193 A | 10/1998 | Singer et al. |
| 5,829,441 A | 11/1998 | Kidd et al. |
| 5,868,138 A | 2/1999 | Halstrom |
| 6,041,784 A | 3/2000 | Halstrom |
| 6,152,138 A | 11/2000 | Brown et al. |
| 6,302,110 B1 | 10/2001 | Yoshida |
| 6,505,628 B2 | 1/2003 | Kittelsen et al. |
| 6,510,853 B1 | 1/2003 | Kittelsen et al. |
| 6,530,375 B1 | 3/2003 | Cieslik, Jr. |
| 6,539,943 B1 | 4/2003 | Kittelsen et al. |
| 6,604,527 B1 | 8/2003 | Palmisano |
| 6,626,180 B1 | 9/2003 | Kittelsen et al. |
| 6,857,429 B2 | 2/2005 | Eubank |
| 6,886,566 B2 | 5/2005 | Eubank |
| 6,983,752 B2 | 1/2006 | Garabadian |
| 7,404,404 B2 | 7/2008 | Lombardi |
| 7,434,582 B2 | 10/2008 | Eubank |
| 7,506,651 B2 | 3/2009 | Anonsen |
| 7,559,328 B2 | 7/2009 | Eubank |
| 7,637,262 B2 | 12/2009 | Bailey |
| 7,654,267 B2 | 2/2010 | Boyd |
| 7,757,693 B2 | 7/2010 | Toussaint |
| 7,832,402 B2 * | 11/2010 | Nelissen ................ A61F 5/566 128/848 |
| 7,954,496 B2 | 6/2011 | Jansheski et al. |
| 7,971,591 B2 | 7/2011 | Jansheski |
| 8,001,972 B2 | 8/2011 | Eubank |
| 8,074,659 B2 | 12/2011 | Hanna |
| 8,166,976 B2 | 5/2012 | Webster et al. |
| 8,196,587 B2 | 6/2012 | Chodorow |
| 8,205,617 B2 | 6/2012 | Scarberry et al. |
| 8,333,202 B2 | 12/2012 | Lyons |
| 8,453,650 B1 | 6/2013 | Frey |
| 8,517,029 B2 * | 8/2013 | Nelissen ........................ 128/848 |
| 8,631,800 B2 | 1/2014 | Lindsay et al. |
| 8,646,455 B2 | 2/2014 | Webster et al. |
| 8,671,946 B2 | 3/2014 | Thornton |
| 8,701,673 B2 | 4/2014 | Chodorow |
| 8,733,364 B2 | 5/2014 | Chodorow |
| 8,763,613 B2 | 7/2014 | Chodorow |
| 8,783,261 B2 | 7/2014 | Thornton |
| 8,882,497 B2 | 11/2014 | Frantz et al. |
| 9,022,903 B2 | 5/2015 | Rafih et al. |
| 2007/0224567 A1 | 9/2007 | Robson |
| 2007/0287598 A1 | 12/2007 | Christensen, III |
| 2008/0000483 A1 | 1/2008 | Halstrom |
| 2009/0090371 A1 | 4/2009 | Toussaint |
| 2009/0165805 A1 | 7/2009 | Syrop et al. |
| 2010/0242970 A1 | 9/2010 | Schmitt-Bylandt |
| 2010/0316973 A1 | 12/2010 | Remmers et al. |
| 2011/0030704 A1 | 2/2011 | Hanna |
| 2013/0220341 A1 | 8/2013 | Scheffel |
| 2014/0020691 A1 | 1/2014 | Sweeney et al. |
| 2014/0060549 A1 | 3/2014 | Lucas |
| 2014/0076332 A1 | 3/2014 | Luco |
| 2014/0090652 A1 | 4/2014 | Hakimi |
| 2014/0109919 A1 | 4/2014 | Crout |
| 2014/0120489 A1 | 5/2014 | Klein et al. |
| 2014/0224259 A1 | 8/2014 | Frey et al. |
| 2014/0224260 A1 | 8/2014 | Frey et al. |
| 2014/0230829 A1 | 8/2014 | Rogers |
| 2014/0238414 A1 | 8/2014 | Lucas |
| 2014/0238415 A1 | 8/2014 | Lucas |
| 2014/0326252 A1 | 11/2014 | Quaka et al. |
| 2014/0332011 A1 | 11/2014 | Turek |
| 2014/0352700 A1 | 12/2014 | Ingemarsson-Matzen |
| 2014/0352701 A1 | 12/2014 | Ingemarsson-Matzen |
| 2015/0000677 A1 | 1/2015 | Magness |
| 2015/0004555 A1 | 1/2015 | Frey et al. |
| 2015/0034093 A1 | 2/2015 | Kruger et al. |
| 2015/0059766 A1 | 3/2015 | Frantz et al. |
| 2015/0101614 A1 | 4/2015 | Quaka et al. |

* cited by examiner

ORAL MOTION PRESERVATION DEVICE

CROSS REFERENCE TO RELATED APPLICATION(S)

This application claims priority to Provisional Application Ser. No. 61/939,586, filed on Feb. 19, 2014, the entirety of which is incorporated by reference as if fully set forth herein.

FIELD

This document relates, generally, to an oral device, and in particular, to an oral device for the preservation of natural mandibular motion and prevention and/or reduction of bruxism.

BACKGROUND

Bruxism generally refers to the excessive grinding and/or gnashing of the teeth, in which the top and bottom teeth forcefully slide against each other, and/or excessive clenching of the jaw. Frequent, severe and/or sustained bruxism may lead to Temporomandibular Joint Syndrome (TMJS) and/or Temporomandibular Joint Disorder (TMJD). Bruxism is an oral para-functional activity, in that it is not typically a conscious action, and not related to normal oral functions such as, for example, eating or talking. Symptoms such as facial pain, neck pain, hypersensitive teeth, aching jaw muscles, headaches and other such symptoms may be associated with bruxism. Bruxism may also cause tooth wear, bite misalignment, and damage and/or breakage of teeth and dental restorations such as crowns and fillings. A device that preserves natural jaw motion while providing a barrier to the underlying teeth, may be effective dissipating forces generated due to grinding and preserving natural motion, while separation of the upper an lower jaws may minimize clenching and related complications and/or symptoms.

SUMMARY

In one aspect, a bruxism device, as embodied and broadly described herein, may include an articulation plate including a plurality of second articulating components and at least one articulating height-adjustable damper, wherein the articulation plate is configured to conform to at least one tooth, and a bite plate including a plurality of first articulating components, wherein the bite plate is adjustably connected to the articulation plate. Each second articulating component may articulately receive a single first articulating component. At least one articulating damper may be adjusted by height in order to space the upper and lower jaws apart.

In another aspect, an oral device, as embodied and broadly described herein, may include a first plate, a second plate, a coupling device configured to couple the first plate and the second, and an articulating coupler configured to allow for articulation between the first plate and the second plate coupled by the coupling device. The articulating coupler may include a plurality of first articulating components included on the first plate, and a plurality of second articulating components included on the second plate and configured to respectively engage with the plurality of first articulating components so as to guide a 360 degree relative motion of the first and second plates.

In another aspect, an oral device, as embodied and broadly described herein, may include a bite plate, an articulation plate, at least one post defined by a protrusion extending outward from a mating surface of the articulation plate, at least one housing defined by a recess in a mating surface of the bite plate, at a position corresponding to the at least one post, so as to receive a distal end of the at least one post therein and couple the articulation plate and the bite plate, at least one first articulating component included on the mating surface of the bite plate, and at least one second articulating component included on the mating surface of the articulation plate, at a position corresponding to the at least one first articulating component, an inner contour of the at least one second articulating component corresponding to an outer contour of the at least one first articulating component.

In some embodiments, a locking wafer positioned between the mating surfaces of the bite plate and the articulation plate, the locking wafer setting a prescribed distance between the mating surfaces of the bite plate and the articulation plate.

In some embodiments, a plurality of locking pins may extend between the bite plate and the articulation plate to fix the bite plate and the articulation plate in a selected position.

In some embodiments, the bite plate may be fitted on a separate oral device positioned on the teeth of one of the upper jaw or the lower jaw.

In some embodiments, the articulation plate may be fitted oral device positioned on the teeth of one of the upper jaw or the lower jaw.

In another aspect, a bruxism device, as embodied and broadly described herein, may include a bite plate including a plurality of first articulating components, an articulation plate including a plurality of second articulating components configured to respectively engage the plurality of first articulating components, and at least one articulating damper included in the articulation plate, wherein a position of the at least one articulating damper is configured to be adjusted in response to an external actuation force applied to the at least one articulating damper so as to adjust a separation distance between an upper jaw received in one of the bite plate or the articulation plate and a lower jaw received in the other of the bite plate or the articulation plate.

The details of one or more implementations are set forth in the accompanying drawings and the description below. Other features will be apparent from the description and drawings, and from the claims.

DETAILED DESCRIPTION

The following detailed description sets forth various exemplary embodiments of a bruxism device. The description is not to be taken in a limiting sense, but is made merely for the purpose of illustrating the general principles as broadly described herein.

An oral bruxism device, as embodied and broadly described herein, may serve as an oral motion preservation device, preserving natural motion of the upper and lower jaws of a patient in the event of grinding and/or gnashing and/or clenching of the jaws. In some embodiments, an oral bruxism device may include a static bite plate positioned between the upper jaw and the lower jaw, and in particular, between the teeth of the upper jaw and the teeth of the lower jaw. This type of static bite plate may provide some protection against wear of the teeth of the upper and/or lower jaws. However, this type of static bite plate may still provide some resistance against the natural movement of the jaws, and thus may still transfer deleterious stress forces generated by a grinding motion onto the underlying teeth as well as the temporomandibular joints and connective soft tissues.

A bruxism device, in accordance with embodiments as broadly described herein, may allow for the natural movement of the jaws and dissipate the stress forces generated by the grinding motion. A bruxism device, as embodied and broadly described herein, may include, for example, a bite plate connected to an articulation plate. The bite plate may include a plurality of first articulating components extending generally perpendicularly from the bite plate. The articulation plate may include an inner material capable of being fit or conformed to the upper jaw or the lower jaw, or conformed to fit a form-fitted, or custom-fitted, dental/oral tray or other type of dental/oral mouth guard. The articulation plate may also include a plurality of second articulating components adapted so that each second articulating component may articulately receive a single one of the plurality of first articulating components included on the bite plate. The bruxism device may be mounted on the upper jaw or the lower jaw. A separation distance between the bite plate and the articulation plate may be adjusted by a damper, so that corresponding teeth may be separated by a predetermined distance from the bruxism device. The damper may be an articulating damper, or a non-articulating damper. When a user wearing the bruxism device grinds his/her teeth, the articulating components may provide a 'gliding' affect for the upper and/or lower jaws, so that the teeth do not encounter significant friction and the jaws do not encounter significant resistance. The non-constrained motion of the upper and lower jaws provided for by a bruxism device as embodied and broadly described herein may allow the jaws to maintain a substantially natural motion state.

Figure 1A:
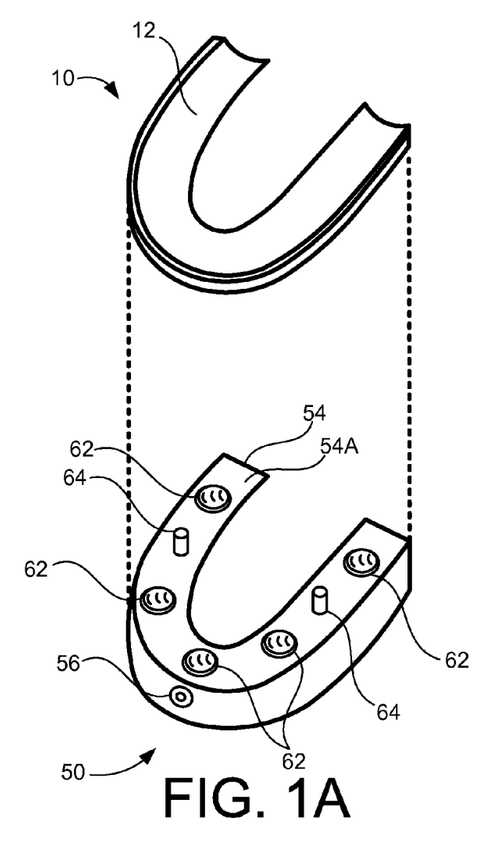
FIG. 1A is a disassembled perspective view of an exemplary bruxism device, in accordance with an embodiment as broadly described herein.

An example implementation of a bruxism device, in accordance with one embodiment, is shown in the disassembled perspective view of FIG. 1A. The bruxism device 100 may include, for example, a first plate 10 selectively coupled to a second plate 50. For ease of discussion, the first plate may hereinafter be referred to as a bite plate 10, and the second plate may hereinafter be referred to as an articulation plate 50.

Figure 1B:
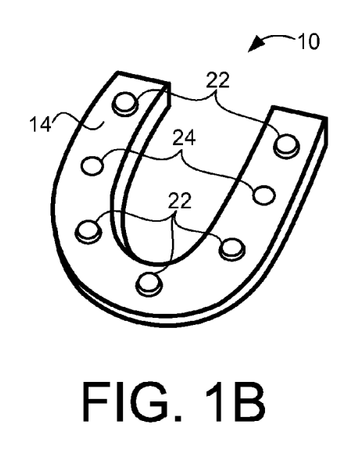
FIG. 1B is a perspective view of an inner side of the first plate of the exemplary bruxism device shown in FIG. 1A, in accordance with an embodiment as broadly described herein.

In some embodiments, the bite plate 10 may include a soft inner lining 12 and a rigid outer lining 14, the inner lining 12 being situated on an inner side of the bite plate 10 in which the teeth of one of the upper jaw or the lower jaw are to be received, and the outer lining 14 defining an outer side of the bite plate 10, facing the articulation plate 50. In some embodiments, the inner lining 12 may be made of a relatively soft, relatively resilient thermoplastic material such as, but not limited to, plastic. Properties of the material of the inner lining 12 may allow the inner lining 12 to conform to the teeth of a user while also cushioning the jaw against impact and teeth-gnashing forces. In some embodiments, the inner lining 12 may conform to, or receive, or be fitted over an oral device 200 (see FIGS. 5C and 5D), such as, for example a pre-existing oral device 200 which the user has positioned on the teeth, such as, for example, whitening trays and the like, which may have been previously customized for a particular user. In some embodiments, the outer lining 14 may be made of a relatively rigid, somewhat resilient thermoplastic material, such as, but not limited to, plastic. The inner lining 12 may be secured to the outer lining 14 by, for example, an adhesive, a lamination process, and the like. In some embodiments, as shown in FIG. 1B, a plurality of first articulating components 22 may extend outward from a surface 14a of the outer lining 14. In some embodiments, the plurality of first articulating components 22 may extend outward from a surface 14a of the outer lining 14 facing the articulation plate 50, and may extend in a direction that is substantially perpendicular to the surface 14a of the outer lining 14. In some embodiments, a plurality of housings 24, or openings 24, or recesses 24, may also be defined in the surface 14a of the outer lining 14.

Figure 1C:
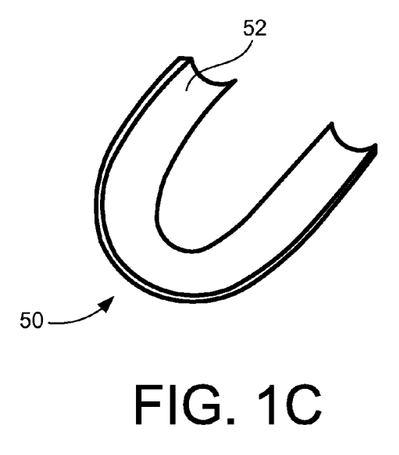
FIG. 1C is a perspective view of an inner side of a second plate of the exemplary bruxism device shown in FIG. 1A, in accordance with an embodiment as broadly described herein.

The articulation plate 50 may be positioned opposite, or facing, the bite plate 10, and may be coupled to the bite plate 10. The articulation plate 50 may include a soft inner lining 52, as shown in FIG. 1C, and a rigid outer lining 54, the inner lining 52 being situated on an inner side of the articulation plate 50 in which the teeth of the other of the upper jaw or the lower jaw are to be received, and the outer lining 54 defining an outer side of the articulation plate 50, facing the bite plate 10. In some embodiments, the inner lining 52 may be made of a relatively soft, relatively resilient thermoplastic material such as, but not limited to, plastic. Properties of the material of the inner lining 52 may allow the inner lining 52 to conform to the teeth while also cushioning the jaw against impact and teeth-gnashing forces. In some embodiments, the inner lining 52 may conform to, or receive, or be fitted over another oral device 200 as described above, which the user has positioned on the teeth, and which may have been previously customized for a particular user, such as, for example, whitening trays and the like. In some embodiments, the outer lining 54 may be made of a relatively rigid, somewhat resilient thermoplastic material, such as, but not limited to, plastic. The inner lining 52 may be secured to the outer lining 54 by, for example, an adhesive, a lamination process, and the like. A plurality of second articulating components 62 and a plurality of posts 64 may be defined on a surface 54a of the outer lining 54 of the articulation plate 50, facing the bite plate 10.

When the bite plate 10 and the articulation plate 50 are coupled, the surface 54a of the articulation plate 50 on which the plurality of second articulating components 62 and the plurality of posts 64 are located may be positioned opposite, or facing, the surface 14a of the outer liner 14 of the bite plate 10 on which the plurality of first articulating components 22 and the plurality of housings 24 are located. The plurality of second articulating components 62 may be engaged with the plurality first articulating components 22 provided on the surface 14a of the bite plate 10. The plurality of posts 64 may be engaged with the plurality of housings 24 defined in the surface 14a of the bite plate 10. The bite plate 10 may interface with the teeth of one of the upper jaw or the lower jaw, and the articulation plate 50 may interface with the teeth of the other of the upper jaw or the lower jaw so as to minimize the transfer of teeth-gnashing forces.

Each housing 24 formed in the surface 14a of the bite plate 10 may be adapted to receive a single, corresponding post 64 of the articulation plate 50. When the posts 64 are received in their respective housings 24, the bite plate 10 and the articulation plate 50 may be coupled. In some embodiments, each post 64 may be fixed in its respective housing 24 by, for example, an adhesive or other attaching material. In some embodiments, each post 64 may be fixed in its respective housing 24 such that a gap is defined between the surface 14a of the bite plate 10 and the surface 54a of the articulation plate 50.

Figure 2A:
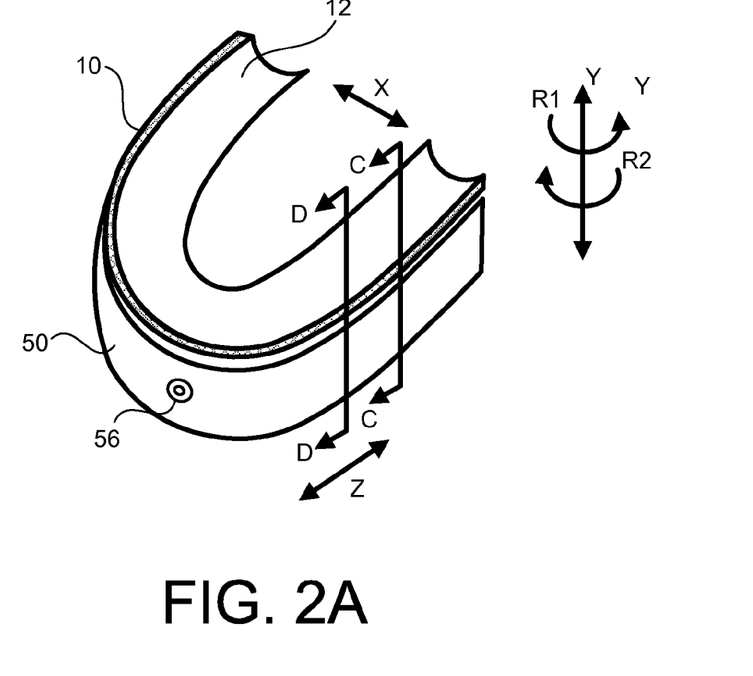
FIG. 2A is an assembled perspective view of the exemplary bruxism device shown in FIGS. 1A-1C, in accordance with an embodiment as broadly described herein.
Figure 2B:
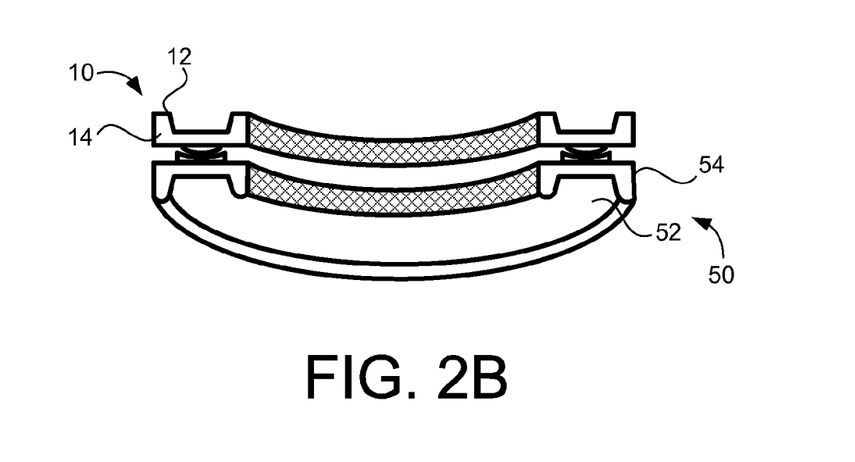
FIG. 2B is a rear view of the exemplary bruxism device shown in FIG. 2A, in accordance with embodiments as broadly described herein.

In the illustrated embodiment, the posts 64 formed on the example articulation plate 50 shown in FIG. 1A have a substantially circular cross section, and extend outward, in a substantially perpendicular direction from the surface 54a of the articulation plate 50 in a substantially cylindrical form. The housings 24, which are formed as recesses in the example bite plate 10 shown in FIG. 1B, also have a substantially circular cross section, extending into the outer lining 14 of the bite plate 10 in a substantially cylindrical form, so as to correspond to the posts 64 and allow the posts 64 to be received and secured in the housings 24. However, in some embodiments, the posts 64 and housings 24 may have other cross sectional shapes. For example, in some embodiments, the posts 64 and housings 24 may have, for example, an elliptical cross section, a square cross section, a rectangular, cross section, or other polygonal cross sectional shape. In some embodiments, a cross sectional shape of the housing 24 corresponds to a cross sectional shape of the post 64 to facilitate insertion and securing of the post 64 in the housing 24. Insertion of one of the posts 64 of the articulating plate 50 into a corresponding housing 24 formed in the bite plate 10 is shown in FIG. 2D.

In some embodiments, the posts 64 may be made of a flexible, somewhat deformable material. Flexibility of the posts 64 fixed in the housings 24 may allow for some movement, such as, for example, longitudinal movement between the bite plate 10 and the articulation plate 50 (in a front and rear direction of the jaws, as shown by the arrow Z in FIG. 2A), and/or transverse movement between the bite plate 10 and the articulation plate 50 (in a right and left direction of the jaws, as shown by the arrow X in FIG. 2A), some compressive movement between the bite plate 10 and the articulation plate 50 (as shown by the arrow Y in FIG. 2A), and/or a combination of the longitudinal and transverse movement which may produce a rotational movement (as shown by the arrows R1 and R2 in FIG. 2A). Flexibility of the posts 64 fixed in the housings 24 and the resulting flexibility in the X, Y, Z, R1 and R2 directions as shown may provide for both shock absorption and stability between the bite plate 10 and the articulation plate 50.

In some embodiments, while being flexible, the posts 64 may also be substantially solid, and relatively free of openings that may otherwise entrap debris and/or moisture, and relatively tightly fitted in the housings to avoid entrapment of debris and/or moisture in spaces between the posts 64 and the housings 24.

Figure 2C:
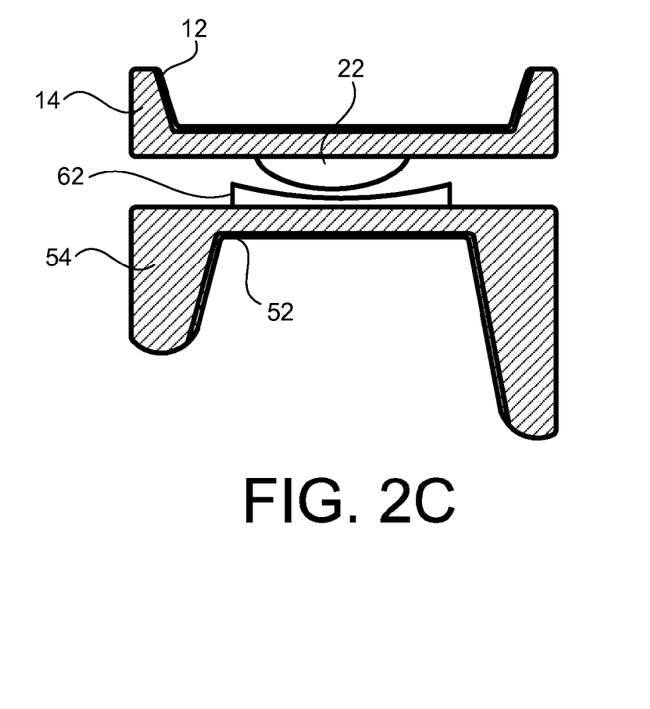
FIG. 2C is a cross sectional view of the exemplary bruxism device taken along line C-C of FIG. 2, illustrating a coupling of a first articulating component and a second articulating component of the exemplary bruxism device, in accordance with an embodiment as broadly described herein.
Figure 2D:
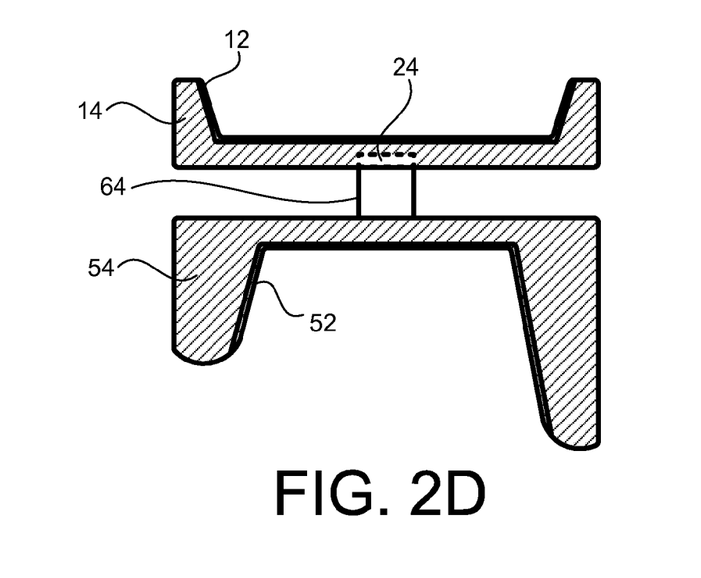
FIG. 2D is a cross sectional view of the exemplary bruxism device taken along line D-D of FIG. 2, illustrating a coupling of a post and a housing of the exemplary bruxism device, in accordance with an embodiment as broadly described herein.

As shown in FIG. 2C, each second articulating component 62 may be adapted to articulately receive, and/or engage with, a single, corresponding first articulating component 22. In some embodiments, the plurality of first articulating components 22 and plurality of second articulating components 62, may, in a received or engaged arrangement, be referred to together as an articulating connector.

In the example embodiment shown in FIGS. 1A-1B and 2C, each of the plurality of first articulating components 22 is defined by a protrusion that extends outward, from the mating surface 14a of the bite plate 10 and having a substantially semispherical shape or surface 22a. In the example embodiment shown in FIGS. 1A-1B and 2C, each of the plurality of second articulating components 62 includes a receiving surface 62a located on the mating surface 54a of the articulation plate 50, at positions corresponding to the positions of the plurality of first articulating components 22. The receiving surface 62a of each of the second articulating components may have a curved, or arcuate, contour, that facilitates essentially 360 degree movement of the semispherical surface 22a of the first articulating component 22 received therein. The curved indentation, or curved recess, formed by the receiving surface 62a allows the first articulating component 22 to be received in and move freely within the second articulating component 62 without becoming easily disengaged.

In some embodiments, the first and second articulating components 22 and 62 may include, for example, ball and trough components, ball-in-socket components, two plates with a mobile/sliding core positioned between the two plates, and other such components that, with the articulating components in an aligned and engaged arrangement, would provide for an articulating relationship between the bite plate 10 and the articulation plate 50.

In the views shown in FIGS. 1A, 2A-2B and 3A-3B, the bruxism device 100 is oriented with the bite plate 10 at an upper portion of the device 100 and the articulation plate 50 at a lower portion of the device 100. When the bite plate 10 and the articulation plate are oriented in this manner, and coupled in the manner shown in FIG. 2, the device 100 may be worn so that the teeth of the upper jaw are received in the inner lining 12 of the bite plate 10, and the teeth of the lower jaw are received in the inner lining 52 of the articulation plate 50, such that the device 100 is essentially "worn" or "mounted" on the upper jaw. The bite plate 10 and articulation plate 50 of the bruxism device 100 are oriented as shown in FIGS. 1A, 2A and 2B simply to facilitate description of the features of the device 100. In some embodiments, the device 100 may be worn in a position inverted from what is shown in FIGS. 1A, 2A-2B and 3A-3B. That is, in some embodiments, the teeth of the bottom jaw may be received in the inner lining 12 of the bite plate 10, and the teeth of the upper jaw may be received in the inner lining 52 of the articulation plate 50, such that the device 100 is essentially "worn" or "mounted" on the lower jaw.

In the example implementation shown in FIGS. 1A-1C, 2A-2D and 3A-3B, the first articulating components 22 and the housings 24 are located on the surface 14a of the bite plate 10, and the second articulating components 62 and the posts 64 are located on the surface 54a of the articulating plate 50. However, in some embodiments, the first articulating components 22 and the housings 24 may be located on the surface 54a of the articulation plate 50, and the second articulating components 62 and the posts 64 may be located on the surface 14a of the bite plate 10. Other various arrangements of the first and second articulating components 22 and 62, the housings 24 and the posts 64 on the surfaces 14a and 54a of the bite plate 10 and the articulating plate 50 may also be implemented, as long as engagement between the first and second articulating components 22 and 62, and between the posts 64 and housings 24, may be maintained. For example, while the illustrated embodiment includes the "male" articulating component 22 on the bite plate 10 and the "female" articulating component 62 on the articulation plate 50, respective installation of the articulating components 22 and 62 on the bite plate 10 and the articulation plate 50 may be reversed, for some, or for all, of the pairs of articulating components 22/62. Similarly, while the illustrated embodiment includes the "male" post 64 on the articulation plate 50 and the "female" housing 24 in the bite plate 10, respective installation of the housings 24 and posts 64 on the bite plate 10 and the articulation plate 50 may be reversed, for some, or for all, of the pairs of housings 24 and posts 64.

In the illustrated embodiment shown in FIGS. 1A-1C, the bite plate 10 and articulation plate 50 includes two pairs of first and second articulating components 22 and 62 arranged on a first side (for example, a left side) of the bruxism device 100, two pairs of first and second articulating components 22 and 62 arranged on a second side (for example, a right side) of the bruxism device 100, and one pair of first and second articulating components 22 and 62 arranged at a front central portion of the bruxism device 100, or five total pairs of first and second articulating components 22 and 62 movably coupling the bite plate 10 and the articulation plate 50. However, in some embodiments, more, or fewer, pairs of first and second articulating components 22 and 62 may be arranged along the mating surfaces of the bite plate 10 and the articulation plate 50, depending, for example, on a size of the bruxism device, and amount of correction and/or compensation required, and other such factors.

In some embodiments, an articulating damper 56 may be provided in, for example, the articulating plate 50. The articulating damper 56 may include a mechanism that adjusts and maintains a desired position between the bite plate 10 and the articulation plate 50, and thus a desired amount of separation between the corresponding teeth of the upper jaw and the lower jaw. In some embodiments, the articulating damper 56 may be included at a front portion of the articulation plate 50, so that the articulating damper 56 is easily accessible and may provide for adjustment of the separation distance between the front teeth, which may facilitate the further dissipation of grinding and clenching forces. In some embodiments, this separation distance may be between approximately 0.0 mm and 50.0 mm, depending, for example, on the size of a particular bruxism device and/or the individual needs and/or comfort of a particular user.

Figure 3A:
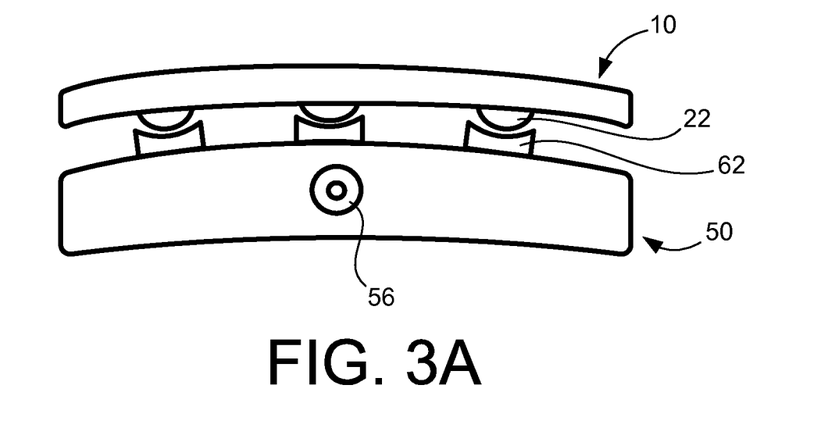
FIGS. 3A-3C are front assembled views of a bruxism device, in accordance with embodiments as broadly described herein.
Figure 3B:
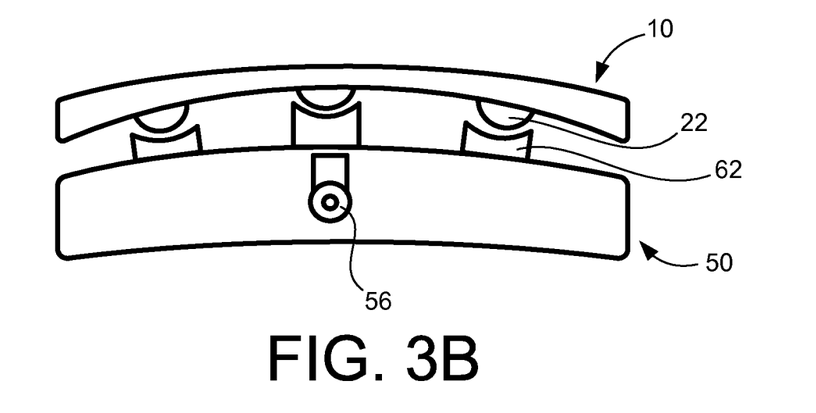

FIG. 3A is a front view of the exemplary bruxism device 100, in which the articulating damper 56 has not been actuated. In the example shown in FIG. 3B, the articulating damper 56 is provided at a front, or anterior, portion of the device 100, and has been actuated to increase a separation distance, or damper opening, between the front teeth received in the bite plate 10 and the front teeth received in the articulation plate 50. The articulating damper 56 may employ, for example, a cam, a spring, a piston, a jack, a wedge and the like to generate and maintain the separation distance, and may be adjusted by, for example, a knob, a hex key, a button and the like. In some embodiments, the articulating damper 56 may exert a force on an underside of the outer lining 54, pushing the surface 54a in the direction of the surface 14a, and consequently increasing a separation distance between the teeth received in the articulation plate 50 and the bite plate 10 in the general area of the damper 56. In some embodiments, this force exerted by the articulating damper 56 may be exerted on a corresponding one of the second articulating components 62. In other embodiments, actuation may cause a portion of the damper 56 to extend up through the surface 54a of the articulation plate 50 to push on the surface 14a of the bite plate 10.

Figure 3C:
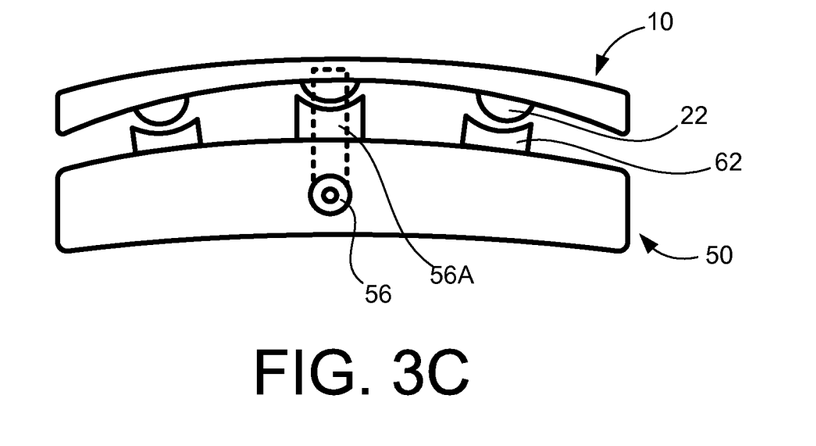

As shown in FIG. 3C, in some embodiments, the damper 56 may be coupled to a riser 56A. In response to actuation of the damper 56, the riser 56A may protrude through an opening in the articulation plate 50 and an opening in the bite plate 10, causing the riser 56A to directly contact the teeth received in the bite plate 10 to maintain a separation distance between the bite plate 10 and the teeth.

Figure 4A:
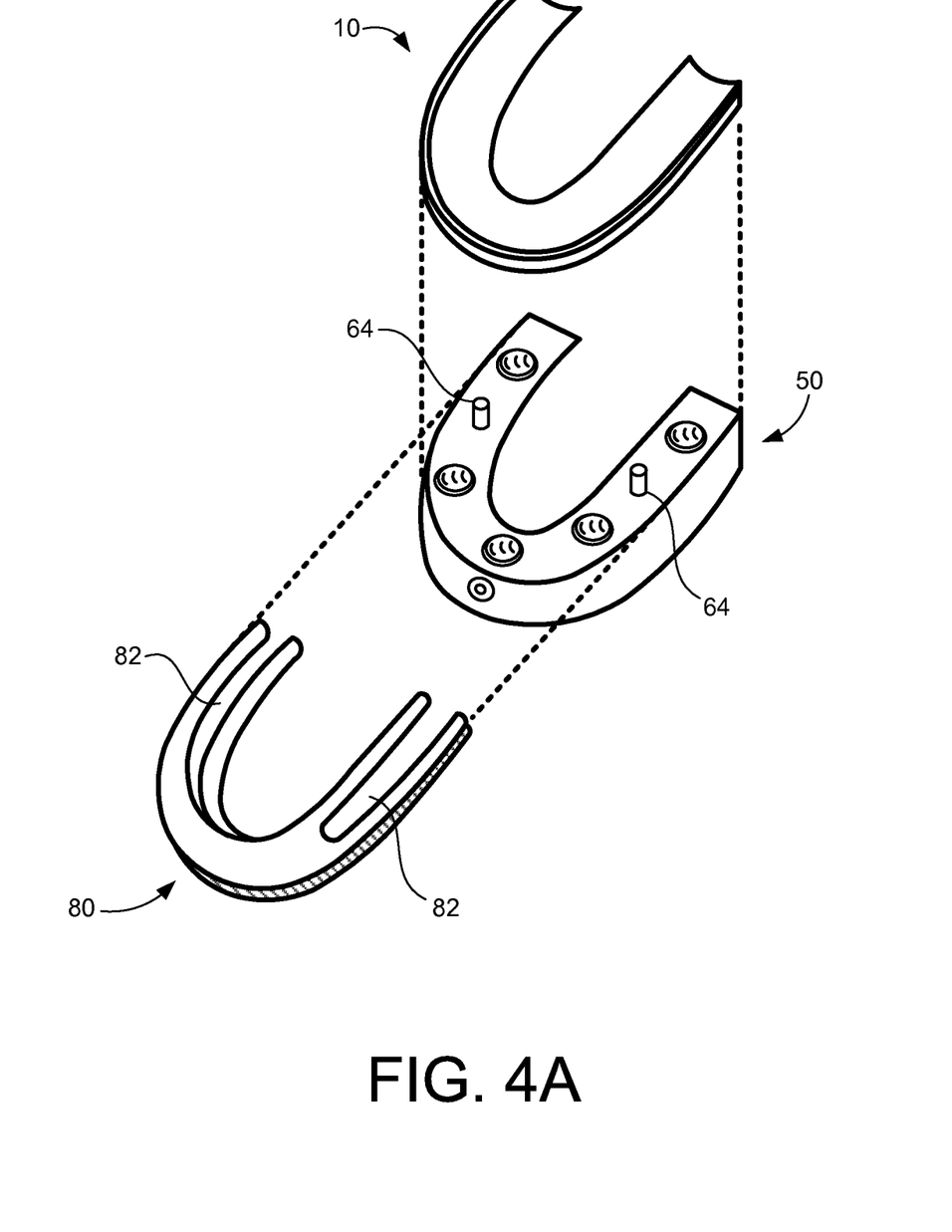
FIGS. 4A-4C are disassembled perspective views of a bruxism device, in accordance with another embodiment as broadly described herein.

In some embodiments, the bite plate 10 and the articulation plate 50 may be secured in a desired position to limit relative movement of the jaws in a particular direction, or to limit relative movement of the jaws to a particular amount. For example, as shown in FIG. 4A, in some embodiments, a locking wafer 80 may be inserted between the bite plate 10 and the articulation plate 50 to secure, or lock, a relative position of the bite plate 10 and the articulation plate 50. The locking wafer 80 may include channels 82 extending longitudinally along opposite side portions of the locking wafer 80. The locking wafer 80 may slide into place on the articulation plate 50, as illustrated by the dotted lines shown in FIG. 4A, with the posts 64 on opposite sides of the articulation plate 50 sliding along the channels 82 on the opposite sides of the locking wafer 80 to guide the locking wafer 80 into position on the articulation plate 50. The locking wafer 80 may remain secured in its position between the bite plate 10 and the articulation plate 50 due to some amount of friction between the locking wafer 80 and the bite plate 10 and/or articulation plate 50, as well as the positioning of the posts 64 in the channels 82.

Figure 4B:
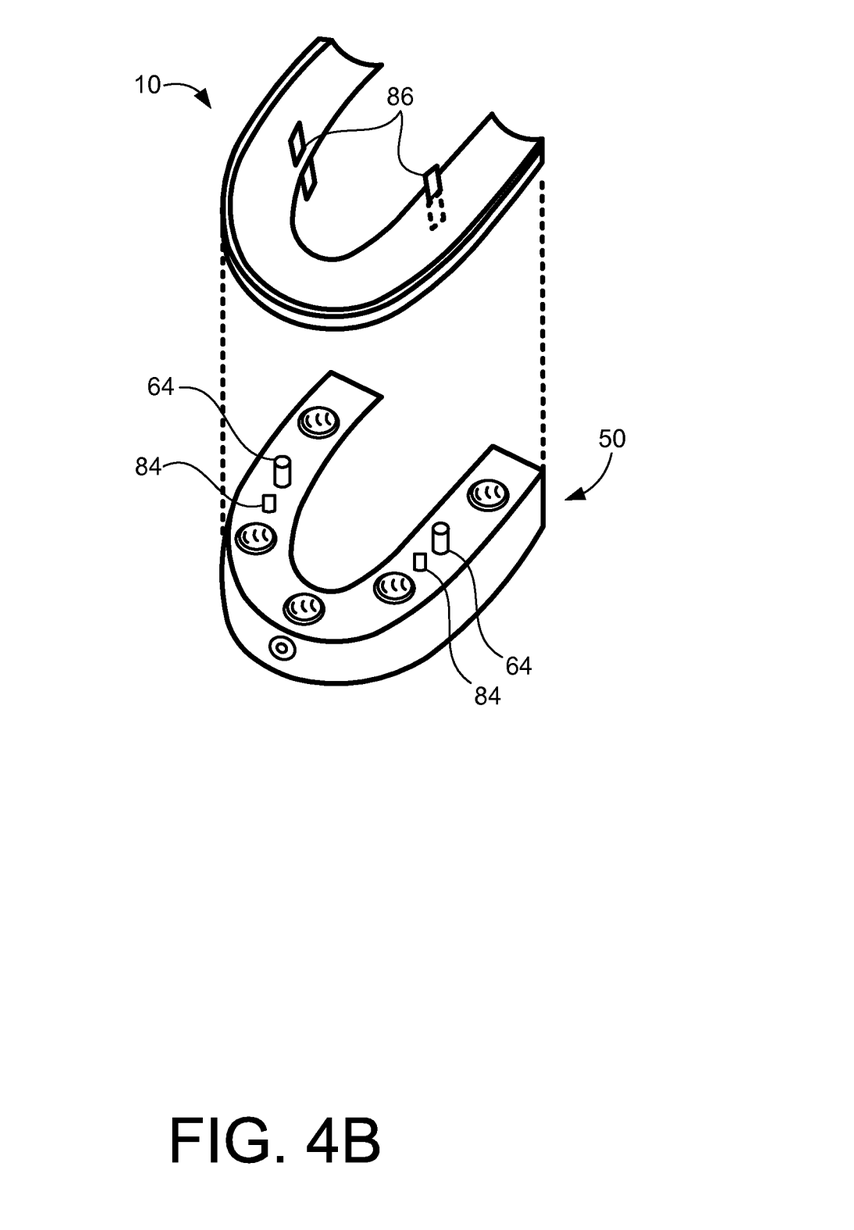

In some embodiments, a plurality of first locking pins 84 and a plurality of second locking pins 86 may secure, or lock, a relative position of the bite plate 10 and the articulation plate 50, as shown in FIG. 4B. In some embodiments, the plurality of first locking pins 84 and/or the plurality of second locking pins 86 may be removable from and insertable into corresponding openings in the articulation plate 50 and the bite plate 10, respectively, so that a desired position of the bite plate 10 and the articulation plate 50 may be selected and secured, and adjusted as necessary. In some embodiments, the plurality of first locking pins 84 and/or the plurality of second locking pins 86 may be, for example, tension mounted so that pressure applied to the first locking pins 84 and/or the second locking pins 86 may cause the first locking pins 84 and/or the second locking pins 86 to be refracted and/or extended.

Figure 4C:
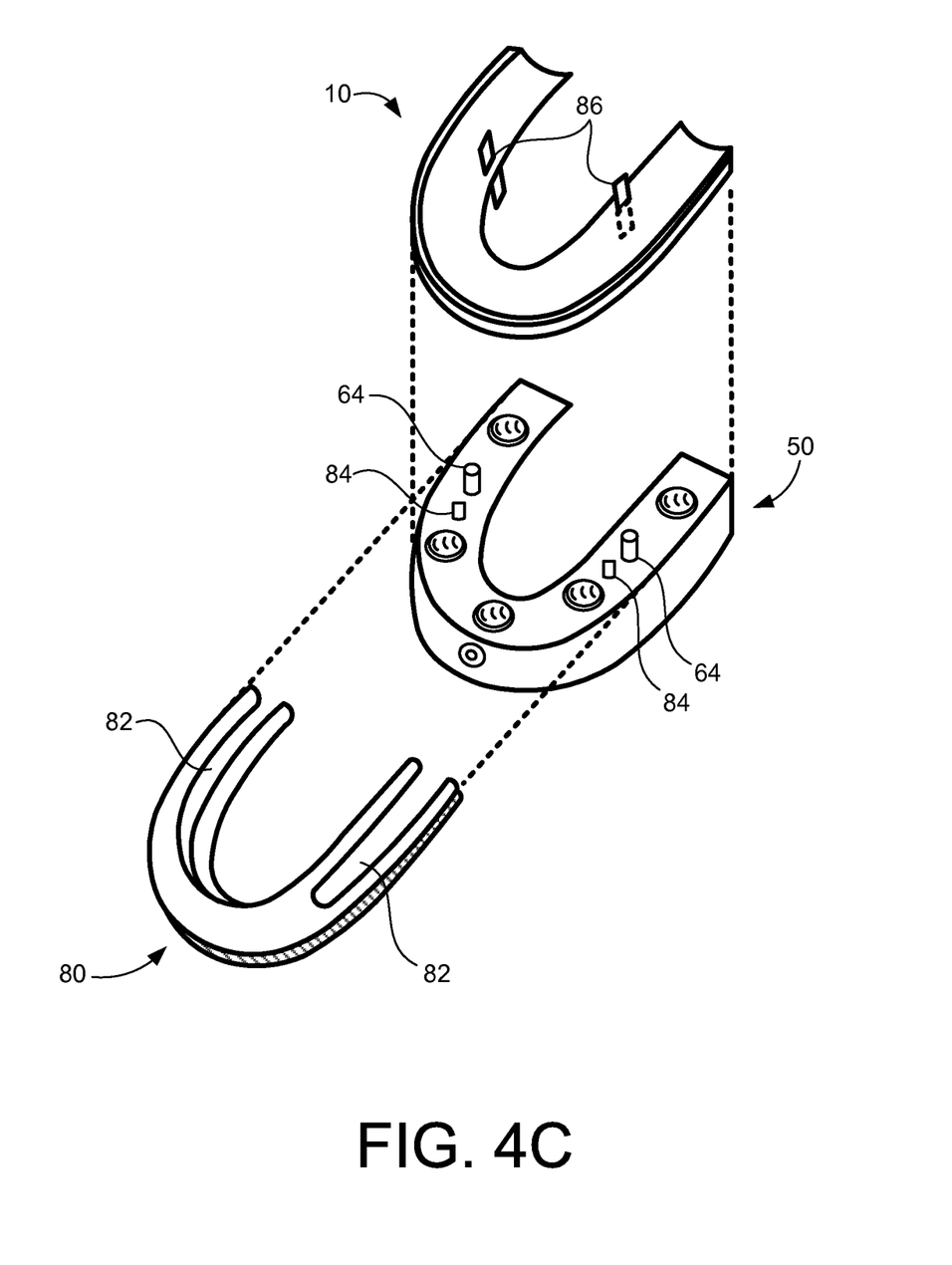

In some embodiments, the bruxism device may include both the locking wafer 80 and the plurality of first locking pins 84 and/or the plurality of second locking pins 86, as shown in FIG. 4C. In this embodiment, as the locking wafer 80 slides into place, the plurality of first locking pins 84 and/or the plurality of second locking pins 86 may extend from the respective bite plate 10 and/or articulation plate 50 for engagement with the locking wafer 80. In this manner, the locking wafer 80 may be positioned and secured between the articulation plate 50 and the bite plate 10 to establish and secure a predetermined position of the articulation plate 50 and the bite plate 10.

Securing, or locking, the articulation plate 50 and the bite plate 10 with either the locking wafer 80 as shown in FIG. 4A, the plurality of first locking pins 84 and/or the plurality of second locking pins 86 as shown in FIG. 4B, or both the locking wafer 80 and the locking pins 84 and/or 86 as shown in FIG. 4C, may cause the device to be in a static, non articulating state, with the bite plate 10 and the articulation plate 50 maintained in a desired relative position.

Figure 5A:
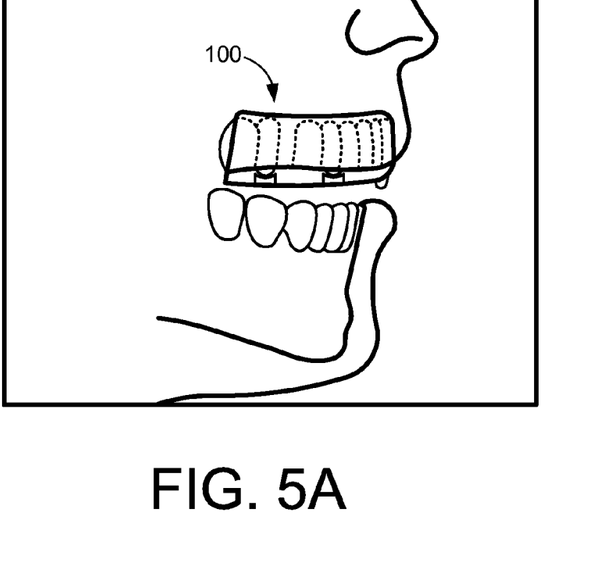
FIGS. 5A-5D illustrate bruxism devices worn by a user, in accordance with embodiments as broadly described herein.
Figure 5B:
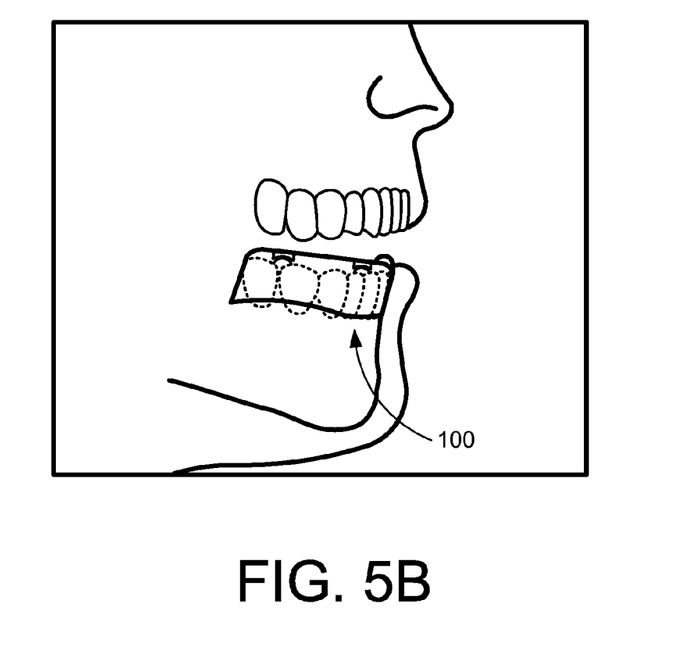

In use, as shown in FIG. 5A, the bruxism device 100 may be worn, or mounted, on the upper jaw, with the teeth of the lower jaw received in the inner lining 52 of the articulation plate 50 when the jaws are in a closed position. As shown in FIG. 5B, the bruxism device 100 may be worn, or mounted, on the lower jaw, with the teeth of the upper jaw received in the inner lining 12 of the bite plate 10 when the jaws are in the closed position. The bruxism device 100 may be available in a variety of sizes, such as, for example, small, medium, large, youth, adult and the like, so that the bruxism device 100 may be adapted to a vast majority of jaw sizes.

Figure 5C:
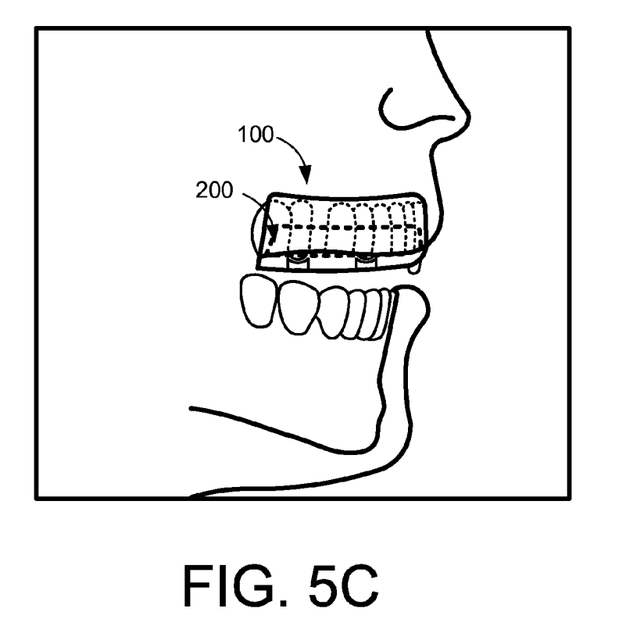
Figure 5D:
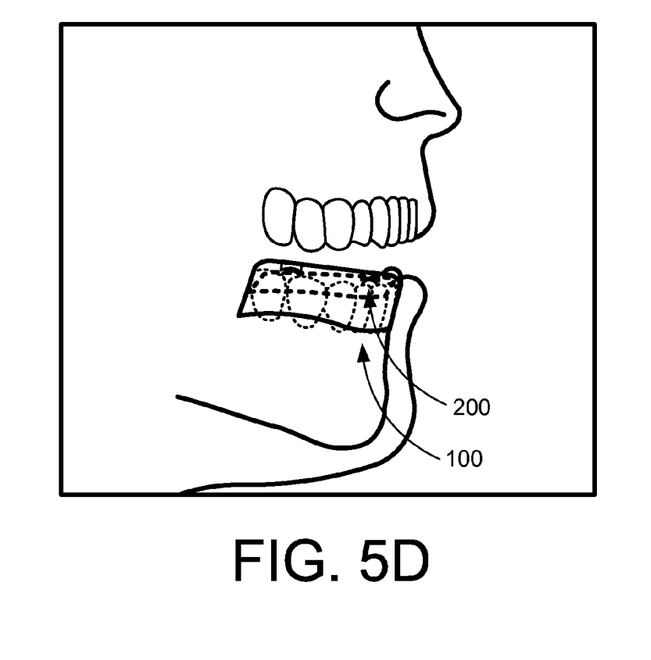

In use, as shown in FIG. 5C, the bruxism device 100 may be worn, or mounted, on the upper jaw, with a separate oral tray 200 positioned on the teeth of the lower jaw, and the separate oral tray 200 being received in, or fitted in, the inner lining 52 of the articulation plate 50 when the jaws are in a closed position. As shown in FIG. 5D, the bruxism device 100 may be worn, or mounted, on the lower jaw, with the separate oral tray 200 on the teeth of the upper jaw, and the separate oral tray 200 being received in, or fitted in, the inner lining 12 of the bite plate 10 when the jaws are in the closed position. As noted above, the bruxism device 100 may be available in a variety of sizes, to adapt to the vast majority of jaw sizes and/or to accommodate various different types of separate, customized trays which the user may already have on hand.

In some embodiments, an impression of the relevant mouth cavity may be taken, and then one or both of the plates may be conformed to the impression. Thereafter, the articulating damper 56 may be actuated to adjust and set an amount of separation between the articulation plate 50 and the bite plate 10 that will yield the desired amount of separation between the corresponding teeth of the upper and lower jaws. The bruxism device 100 may then be mounted to either the upper jaw, as shown in FIG. 4A, or the lower jaw, as shown in FIG. 4B. In mounting the bruxism device 100 to the upper jaw, the teeth of the upper jaw may be received in, for example, the inner lining 52 of the articulation plate 50, so that, when the jaws are in the closed position, the teeth of the lower jaw are received in the inner lining 12 of the bite plate 10. Similarly, in mounting the bruxism device 100 to the lower jaw, the teeth of the lower jaw may be received in, for example, the inner lining 52 of the articulation plate 50, so that, when the jaws are in the closed position, the teeth of the upper jaw are received in the inner lining 12 of the bite plate 10.

In some embodiments, the bruxism device 100 may be customized by the user so that the bite plate 10 and/or the articulation plate 50 may be custom fitted to the particular user's teeth and jaws. For example, in some embodiments, the bite plate 10 and/or the articulation plate 50 may be heated and then positioned in place on the user's teeth/jaws, so that the material of the inner lining 12 of the bite plate 10 and/or the material of the inner lining 52 of the articulation plate 50 may be molded to conform to the user's teeth and jaws. This customized, conformal shape of the inner lining 12 and/or the inner lining 52 may then set as the inner lining 12 and/or the inner lining 52 cools. In some embodiments, this type of customization may be done by the user, providing a less expensive and faster customized solution than a custom device made from impressions taken by a dental professional.

As noted above, in some embodiments, the bite plate 10 and/or the articulation plate 50, and in particular the inner lining 12 of the bite plate 10 and/or the inner lining 52 of the articulation plate 50, may be adapted to receive another type of oral device and/or tray 200 that a user may already have on hand, such as, for example, night guard trays or whitening trays, orthodontic trays, and other such oral devices that may have been previously customized for the user which the user may wish to wear in conjunction with the bruxism device 100. In this instance, the customized tray(s) 200 may be worn on the teeth, and then the bruxism device 100 may be worn over the tray(s) 200. This may allow the user to benefit from previous customization of the tray(s) 200, continue the treatment intended by the tray(s) 200, and still reap the additional benefits provided by the bruxism device 100.

A bruxism device 100, as embodied and broadly described herein, may enable articulating movement of the upper and lower jaws in any number of different directions due to, for example, the essentially 360 degree motion supported by the plurality of first articulating components respectively engaged with the plurality of second articulating components, together with the flexibility and multiple degrees of freedom of motion supported by the plurality of flexible posts 64 respectively received in the plurality of housings 24. Thus, when wearing the bruxism device 100, if clenching does occur, the jaw may articulate in a manner corresponding to its naturally intended movement and dissipate forces on the temporomandibular joint, with the distance between certain teeth of the upper and lower jaws spaced a predetermined distance apart due to the height adjustment provided by the articulating damper 56, rather than remaining in a static clenched state in which damage to the joints and connective tissue may occur. Moreover, when wearing the bruxism device 100, if grinding does occur, the jaw may experience a "gliding" effect due to the plurality of first and second articulating components 22 and 62, without encountering the friction and/or resistance normally encountered when grinding, maintaining the jaws in a natural motion state and avoiding the typical wear, pain and damage normally associated with grinding.

The foregoing provides a detailed description of various exemplary embodiments. It is understood that modifications may be made without departing from the spirit and scope as broadly described herein and as set forth in the following claims.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components, and/or features of the different implementations described.

What is claimed is:
1. An oral device, comprising:
a first plate;
a second plate;
a coupling device, including:
  a first post having a solid cross section, the first post having a first end portion fixedly coupled to one of the first plate or the second plate, and a second end portion fixedly coupled to a first housing defined in the other of the first plate or the second plate; and
  a second post having a solid cross section, the second post having a first end portion fixedly coupled to one of the first plate or the second plate, and a second end portion fixedly coupled to a second housing defined in the other of the first plate or the second plate; and an articulating coupler configured to allow for articulation between the first plate and the second plate coupled by the coupling device, the articulating coupler including:
a plurality of first articulating components included on the first plate; and
a plurality of second articulating components included on the second plate and configured to respectively engage with the plurality of first articulating components so as to guide a relative motion of the first and second plates.

2. The oral device of claim 1, wherein
the first and second posts each extend outward from and substantially perpendicular to a mating surface of the second plate facing the first plate, and the first and second housings are each defined by a respective recess in a mating surface of the first plate facing the second plate.

3. The oral device of claim 2, wherein
a cross sectional shape of the first post corresponds to a cross sectional shape of the first housing and a cross sectional shape of the second post corresponds to a cross sectional shape of the second housing.

4. The oral device of claim 3, wherein the first post and the second post are each made of a flexible material so as to allow for six degree of freedom movement between the first and second plates within a range of motion of the first post and the second post.

5. The oral device of claim 1, wherein each of the first articulating components includes a protrusion having a substantially semispherical shape extending outward from a mating surface of the first plate toward a mating surface of the second plate in the coupled state of the first and second plates.

6. The oral device of claim 5, wherein each of the second articulating components includes a receiving surface having a concave curved contour so as to interact with the semispherical shape of the first articulating component and guide a 360 relative motion between the first and second plates.

7. The oral device of claim 1, further comprising a damper included in one of the first plate or the second plate, wherein the first plate is configured to receive one or more teeth of one of an upper jaw or a lower jaw of a user, and wherein the second plate is configured to receive one or more teeth of the other of the upper jaw or the lower jaw of the user, and wherein the damper includes a cam provided in the one of the first plate or the second plate and configured to impart a separating force on a mating surface of the other of the first plate or the second plate in response to an external actuation force applied to the damper, the separating force increasing a distance between the mating surface of the other of the first plate or the second plate and the at least one tooth received in the one of the first plate or the second plate while the device is worn.

8. The oral device of claim 1, wherein the first plate is a bite plate including a deformable inner liner received in a rigid outer liner, and the second plate is an articulation plate including a deformable inner liner received in a rigid outer liner, wherein the deformable inner liner of the articulation plate is configured to receive one of an upper jaw or a lower jaw of a user, and the deformable inner liner of the bite plate is configured to receive the other of the upper jaw or the lower jaw of the user, a surface of the rigid outer liner of the bite plate and a surface of the rigid outer liner of the articulation plate defining mating surfaces of the first and second plates on which the plurality of first articulating components and plurality of second articulating components are respectively located.

9. The oral device of claim 8, wherein the deformable inner liner of the articulation plate is configured to conform to one or more teeth of the one of the upper jaw or the lower jaw of the user or to a separate oral tray configured to be positioned on the one or more teeth of the one of the upper jaw or the lower jaw, and the deformable inner liner of the bite plate is configured to conform to one or more teeth of the other of the upper jaw or the lower jaw of the user or to a separate oral tray configured to be positioned on the one or more teeth of the other of the upper jaw or the lower jaw.

10. An oral device, comprising:
a bite plate;
an articulation plate;
at least one post having a first end being fixedly coupled to the articulation plate and a second end being fixedly coupled to the bite plate to couple the articulation plate and the bite plate;
at least one first articulating component included on a mating surface of the bite plate; and
at least one second articulating component included on a mating surface of the articulation plate, at a position corresponding to the at least one first articulating component, an inner contour of the at least one second articulating component corresponding to an outer contour of the at least one first articulating component.

11. The oral device of claim 10, wherein the at least one post comprises a solid protrusion made of a flexible material and having a solid cross section, with the distal end of the at least one post being fixedly coupled in at least one housing defined as a recess in the mating surface of the bite plate so as to allow for six degree of freedom movement between the bite plate and the articulation plate within a range of motion of the at least one post, and wherein a cross sectional shape of the at least one housing corresponds to a cross sectional shape of the at least one post.

12. The oral device of claim 11, wherein the at least one first articulating component includes a protrusion that extends outward from the mating surface of the bite plate, the protrusion having a semispherical contour, and the at least one second articulating component includes a receiving surface that engages the semispherical protrusion of the at least one first articulating component, a contour of the receiving surface being defined by a concave curved shape in which the semispherical protrusion of the at least one first articulating component is received.

13. The oral device of claim 12, wherein the concave curved shape of the at least one second articulating component allows for 360 degree relative movement between the bite plate and the articulation plate and prevents disengagement of the at least one first articulating component from the at least one second articulating component.

14. The oral device of claim 10, wherein the articulation plate includes a deformable inner liner received in a rigid outer liner, the deformable inner liner of the articulation plate being configured to receive and conform to one or more teeth of one of an upper jaw or a lower jaw of a user, and the bite plate includes a deformable inner liner received in a rigid out liner, the deformable inner liner of the bite plate being configured to receive and conform to one or more teeth of the other of the upper jaw or the lower jaw of the user.

15. The oral device of claim 10, wherein the at least one post comprises a plurality of posts defined by a plurality of protrusions extending outward from the mating surface of the articulation plate and the mating surface of the bite plate includes a plurality of housings at positions respectively corresponding to the plurality of posts, and the at least one first articulating component comprises a plurality of first articulating components included on the bite plate and the at least one second articulating component comprises a plurality of second articulating components included on the articulation plate at positions respectively corresponding to the plurality of first articulating components.

16. The oral device of claim 10, further comprising an adjustment device coupled to at least one of the bite plate or the articulation plate, the adjustment device including at least one of:
   a locking wafer positioned between the mating surfaces of the bite plate and the articulation plate, the locking wafer setting a prescribed distance between the mating surfaces of the bite plate and the articulation plate; or
   a plurality of locking pins that extend between the bite plate and the articulation plate to fix the bite plate and the articulation plate in a selected position.

17. The oral device of claim 10, further comprising:
   wherein the bite plate is configured to receive one or more teeth of one of an upper jaw or a lower jaw of a user, and wherein the articulation plate is configured to receive one or more teeth of the other of the upper jaw or the lower jaw of the user,
   at least one articulating damper included in the articulation plate, positioned at a central anterior end portion of the articulation plate,
   wherein a position of a bumper of the at least one articulating damper is configured to be adjusted in response to an external actuation force applied to the at least one articulating damper so as to adjust a separation distance between the teeth, at a position corresponding to the bumper, of an upper jaw received in one of the bite plate or the articulation plate, and teeth, at a position corresponding to the bumper, of a lower jaw received in the other of the bite plate or the articulation plate while the device is worn.

18. The device of claim 17, wherein the at least one articulating damper includes a cam provided in one of the bite plate or the articulation plate, wherein the cam is configured to extend the bumper in response to an external actuation of the cam, and wherein, in the extended state, the bumper is configured to impart a separating force on a mating surface of the one of the bite plate or the articulation plate so as to increase a distance between the mating surface of the one of the bite plate or the articulation plate and the teeth therein at the position corresponding to the bumper while the device is worn.

19. The device of claim 17, wherein the articulation plate has a U shaped contour including:
   a first lateral section;
   a second lateral section; and
   a curved section connecting a distal end portion of the first lateral section and a distal end portion of the second lateral section,
   wherein the at least one articulating damper is positioned at a central portion of the curved section of the articulation plate.

20. The device of claim 17, wherein the positioning of the at least one articulating damper at the central anterior end portion of the articulation plate allows the position of the bumper to be adjusted, and the separation distance between teeth at the anterior end portion of the upper jaw and teeth at the anterior end portion of the lower jaw to be adjusted, while the device is worn on the upper jaw and the lower jaw.

21. The oral device of claim 10,
   the articulation plate including:
      a first lateral section;
      a second lateral section;
      a curved section connecting a distal end portion of the first lateral section and a distal end portion of the second lateral section; and
      a single articulating damper included in the curved section of the articulation plate.

22. The device of claim 21, wherein the bite plate is configured to receive one or more teeth of one of an upper jaw or a lower jaw of a user, and wherein the articulation plate is configured to receive one or more teeth of the other of the upper jaw or the lower jaw of the user, the articulating damper including:
   a cam; and
   a bumper, a position of the bumper being adjusted in response to an external force applied to the cam so as to adjust a position of teeth received in the central portion of the curved section of the articulation plate and teeth received in a corresponding portion of the bite plate coupled to the articulation plate while the device is worn.

* * * * *

UNITED STATES PATENT AND TRADEMARK OFFICE
CERTIFICATE OF CORRECTION

PATENT NO. : 9,339,410 B2  
APPLICATION NO. : 14/622024  
DATED : May 17, 2016  
INVENTOR(S) : Brian Francis Smith Page 1 of 1

It is certified that error appears in the above-identified patent and that said Letters Patent is hereby corrected as shown below:

In the Specification

In column 1, line 7, delete "19," and insert -- 13, --, therefor.

In the Claims

In column 13, line 29, in claim 17, delete "the teeth," and insert -- teeth, --, therefor.

Signed and Sealed this  
Second Day of August, 2016

Michelle K. Lee  
*Director of the United States Patent and Trademark Office*